United States Patent [19]

Hackman et al.

[11] Patent Number: 5,766,213
[45] Date of Patent: Jun. 16, 1998

[54] ARCING AND EXPANDING ABSORBENT

[75] Inventors: Sandy Hackman, Somerset, N.J.;
Christopher Holliday, Levittown, Pa.;
Kenneth Pelley, Hopewell, N.J.

[73] Assignee: McNeil-PPC, Inc., Skillman, N.J.

[21] Appl. No.: 705,085

[22] Filed: Aug. 29, 1996

Related U.S. Application Data

[63] Continuation of Ser. No. 332,012, Oct. 31, 1994, abandoned.

[51] Int. Cl.$^6$ ............................................. A61F 13/16
[52] U.S. Cl. ............................. 604/385.1; 604/385.2
[58] Field of Search .................................. 604/369, 374, 604/385.1, 385.2, 386, 387

[56] References Cited

U.S. PATENT DOCUMENTS

| | | | |
|---|---|---|---|
| 3,776,233 | 12/1973 | Schaar | 604/374 |
| 3,848,599 | 11/1974 | Schaar | 604/374 |
| 4,554,191 | 11/1985 | Korpman | 604/389 |
| 4,758,241 | 7/1988 | Papajohn | 604/387 |
| 5,013,309 | 5/1991 | Baigas, Jr. et al. | 604/368 |

FOREIGN PATENT DOCUMENTS 9301785  2/1993  WIPO ................ 604/385.1

*Primary Examiner*—Randy C. Shay

[57] ABSTRACT

An absorbent article useful for wearing in the crotch portion of an undergarment is disclosed. The article has an absorbent structure disposed between a liquid-pervious, body-facing surface and a resilient, liquid-impervious, controlled-deformation shell. The shell has a pair of lateral sides, a garment-facing surface and a peripheral edge. Proximate the peripheral edge of the shell, there is a body-gasketing portion. The shell also has means for adjusting the length of the garment-facing surface and lateral sides. Thus, the garment-facing surface and lateral sides can expand or contract to relieve stresses induced by curving the article while allowing the body-gasketing portion to remain substantially free of folds and gaps.

32 Claims, 5 Drawing Sheets

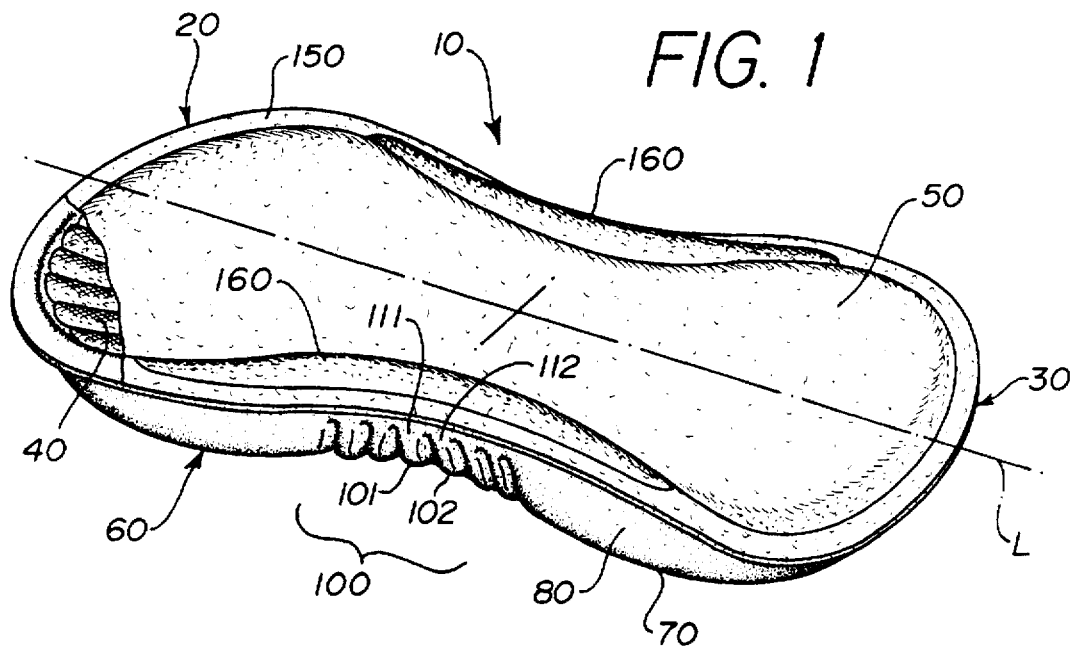
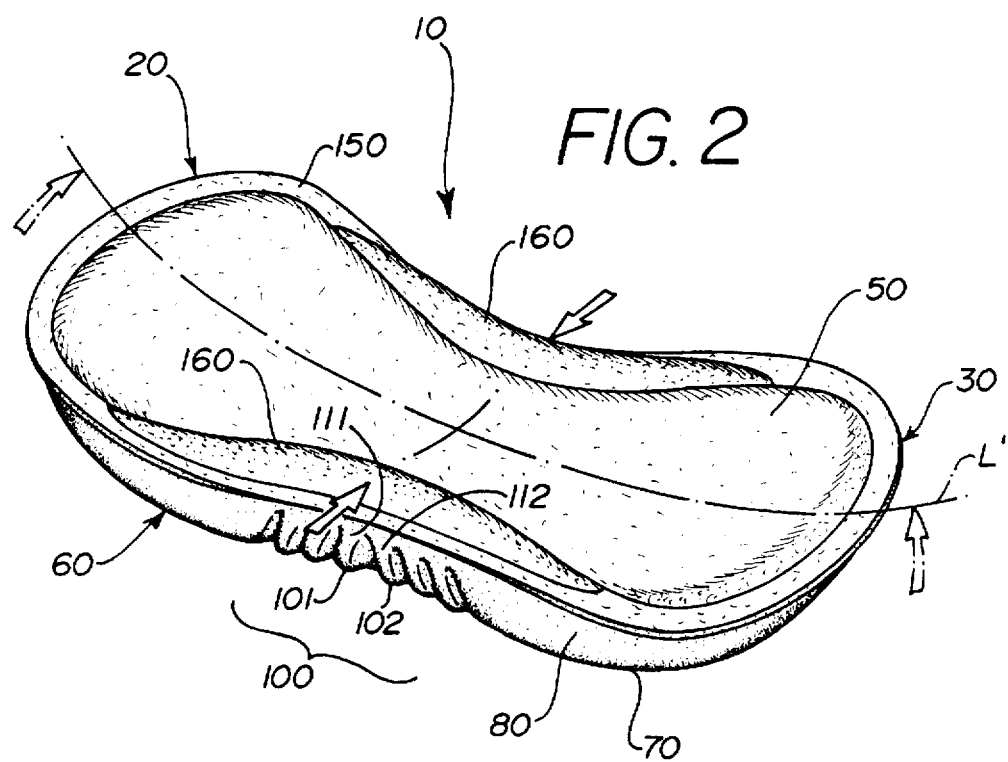

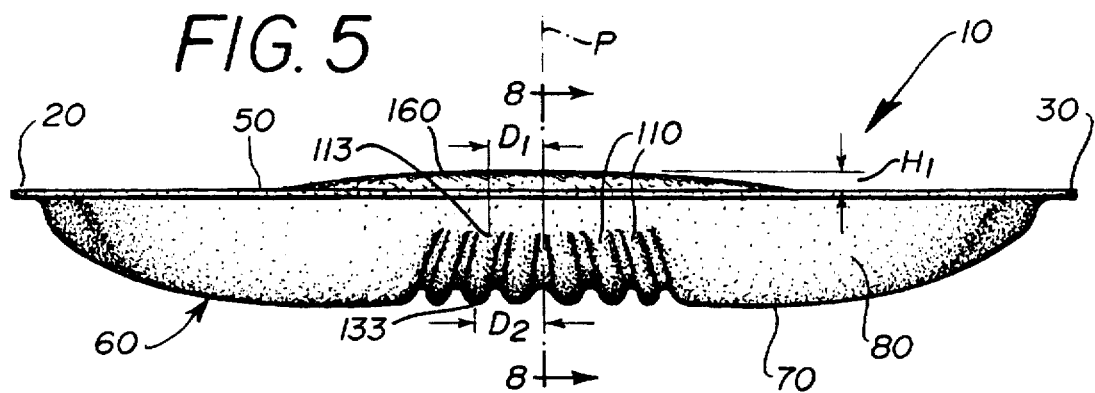
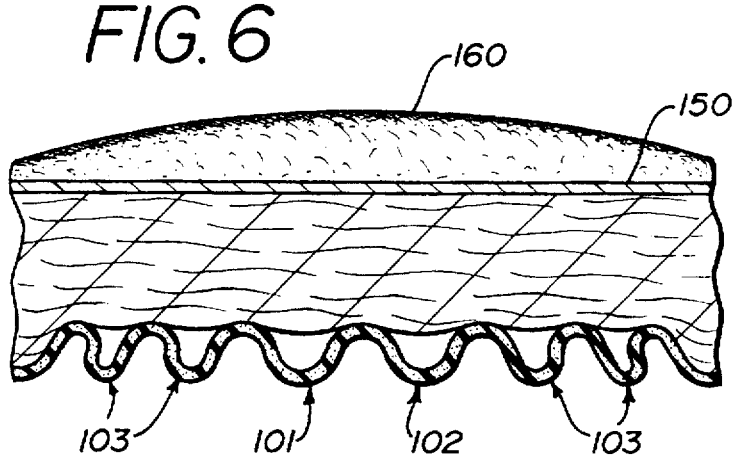
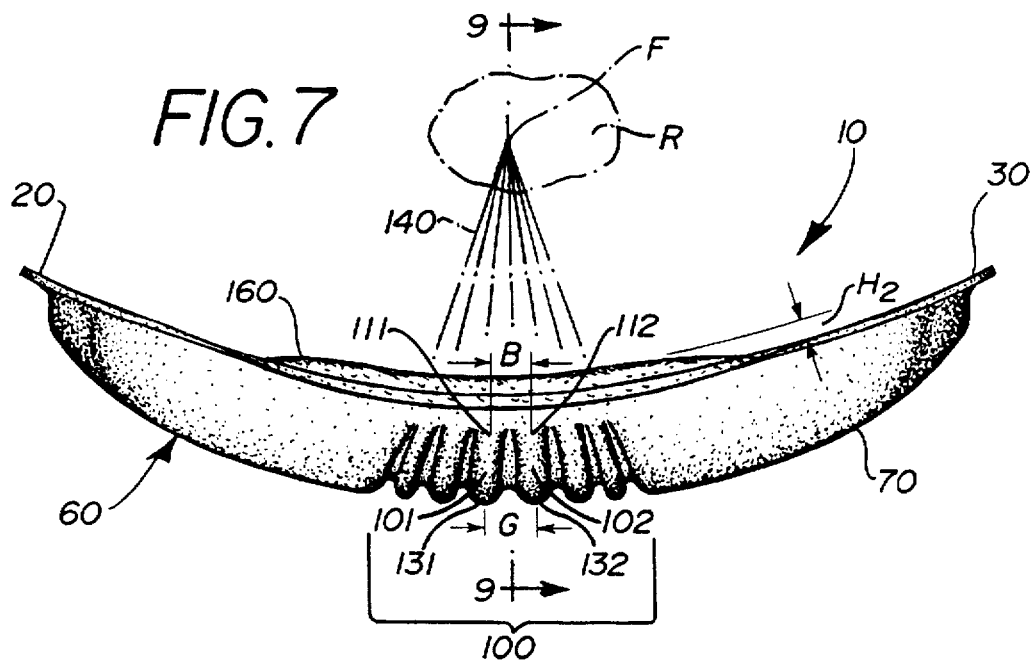

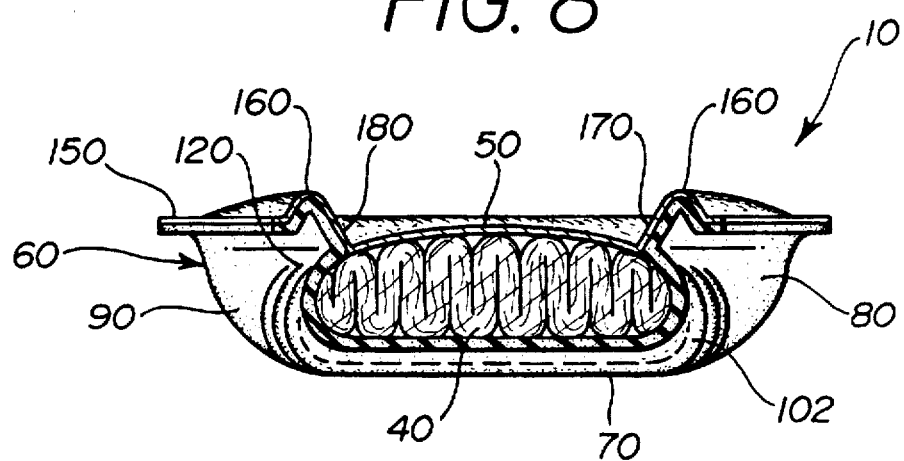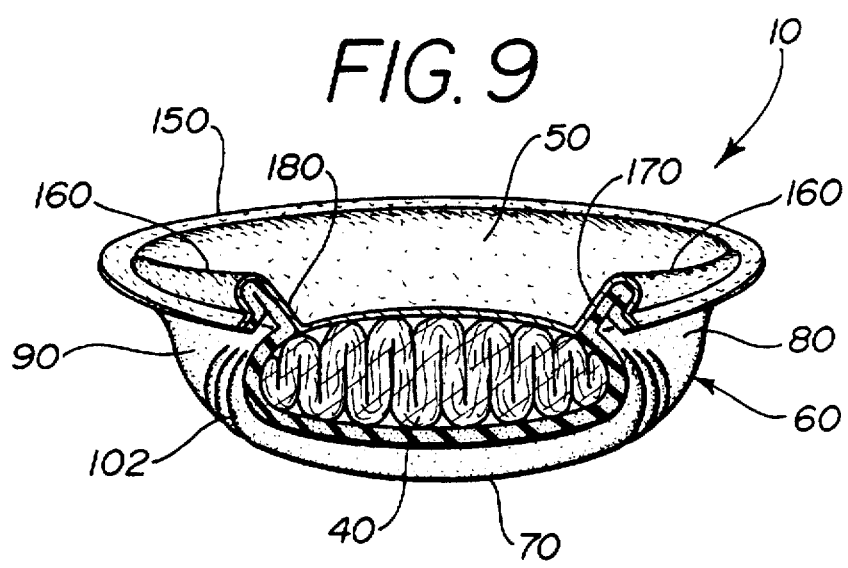

ARCING AND EXPANDING ABSORBENT

This is a continuation of application Ser. No. 08/332,012, filed Oct. 31, 1994, now abandoned.

FIELD OF THE INVENTION

The present invention relates to absorbent articles useful for wearing in the crotch portion of a user's garment. In particular, the invention relates to certain structural features in a controlled-deformation shell which improve the performance of such an article.

BACKGROUND OF THE INVENTION

Disposable absorbent articles such as sanitary napkins and adult incontinence pads are generally designed to be worn in the crotch portion of a user's garment and to absorb and to contain body fluids. Incontinence pads require higher liquid capacity as the void volume of incontinent adults is generally greater than menstrual flow. It is also preferable that adult incontinence pads are compact enough to be worn without being noticeable to passers-by.

These requirements as well as others have been substantially met by the incontinence pad of Holtman, U.S. Pat. No. 4,685,914. The disposable urinary pad of Holtman includes a liquid-impermeable, deformation-resistant, flexible shell containing a fibrous absorbent structure. This pad has a large liquid capacity, rapidly accepts and retains relatively large gushes of liquids, and is comfortable to wear. However, the Holtman pad has a permanently curved form which makes manufacture challenging and results in bulky packaging and storage.

Attempts to form curved sanitary napkins include Mokry, U.S. Pat. No. 4,944,735, which uses elastic bands along the side edges to deform an essentially flat structure into a curved absorbent article. However, the sanitary napkins of Mokry generally have a lower liquid capacity than incontinence pads, and the barrier film is generally limp and does not provide the resilient structural support that the Holtman shell provides.

Diapers have been formed using pleated barrier films. Examples of these products include Schaar et al., U.S. Pat. Nos. 3,776,233 and 3,848,549. Again, the limp barrier film does not provide the structural support of resilient shells.

Therefore, there is a need for an absorbent article useful for wearing in the crotch portion of a user's garment which can comfortably curve to fit the user's body while maintaining sufficient resilient structural integrity to resist gapping and resultant side leakage.

SUMMARY OF THE INVENTION

The absorbent articles of this invention are useful for wearing in the crotch portion of a user's undergarment. The article has an absorbent structure disposed between a liquid-pervious, body-facing surface and a liquid-impervious, controlled-deformation shell. The shell has a pair of lateral sides, a garment-facing surface and a peripheral edge. Proximate the peripheral edge of the shell, there is a body-gasketing portion. Preferably, this body-gasketing portion is covered with a liquid-pervious cover. The shell also has means for adjusting the length of the garment-facing surface and lateral sides. Thus, the garment-facing surface and lateral sides can expand or contract to relieve stresses induced by curving the article while allowing the body-gasketing portion to remain substantially free of folds and gaps.

In a preferred embodiment, the means for expanding the garment-facing surface and lateral sides includes a plurality of expandable corrugations have a terminus on one side, radiate toward the garment-facing surface, traverse the garment-facing surface, and have a second terminus on the opposite lateral side. The expandable corrugations have a unique orientation. When phantom lines are extended from the expandable corrugations on the lateral sides of the shell in a direction away from the garment-facing surface, they converge in a region beyond the body-facing surface of the article. These expandable corrugations help to enable the shell to be articulated between a relatively planar form to a curved form having a radius of curvature from a focal point in the convergence region.

BRIEF DESCRIPTION OF THE DRAWING

FIG. 1 is a perspective view of an absorbent article of this invention in a generally planar position.

FIG. 2 is a perspective view of an absorbent article of this invention in a curved position.

FIG. 5 is a side elevational view of an absorbent article of this invention in a generally planar position.

FIG. 6 is a fragmentary cross-sectional view of an absorbent article of this invention showing the configuration of transverse expandable corrugations as taken along line 6—6 of FIG. 3.

FIG. 7 is a side elevational view of an absorbent article of this invention in a curved position.

FIG. 8 is a transverse cross-sectional view of an absorbent article of this invention showing in a generally planar position as taken along line 8—8 of FIG. 5.

FIG. 9 is a transverse cross-sectional view of an absorbent article of this invention showing in a curved position as taken along line 9—9 of FIG. 7.

DETAILED DESCRIPTION OF THE INVENTION

Figure 3:
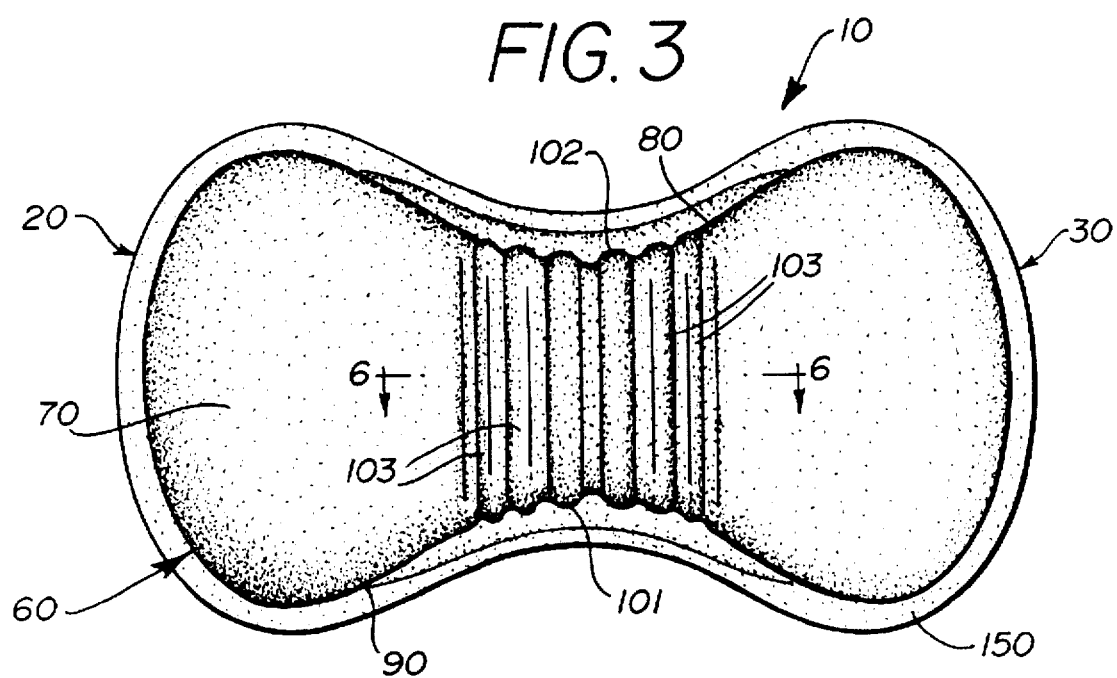
FIG. 3 is a bottom plan view of an absorbent article of this invention in a generally planar position.
Figure 4:
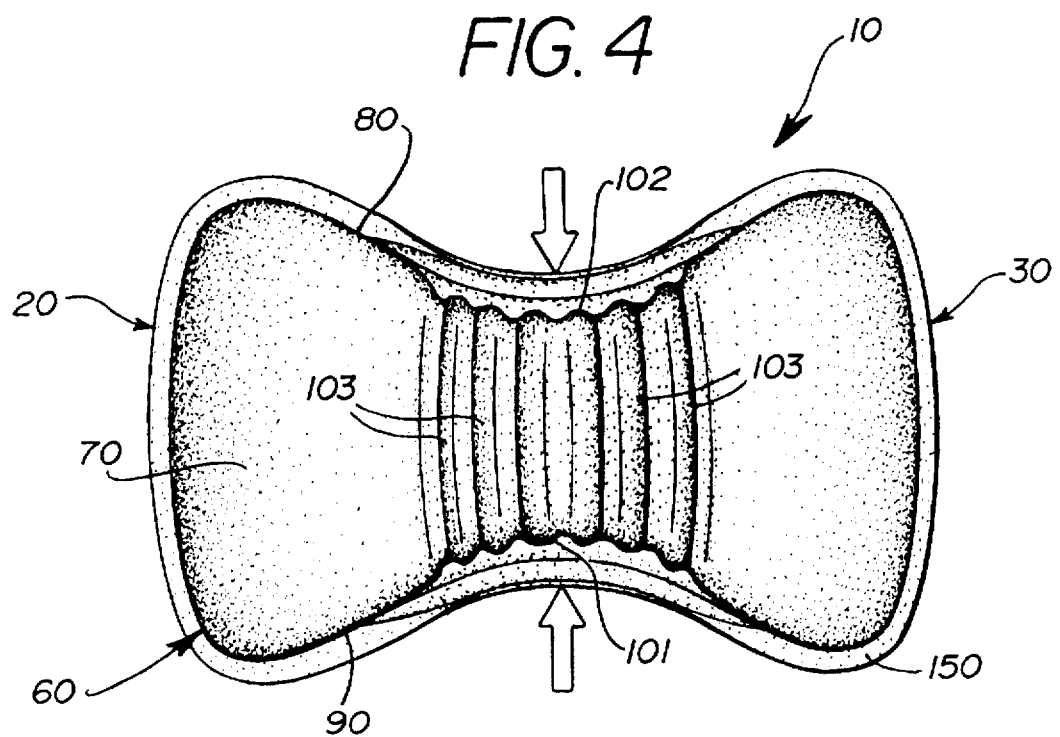
FIG. 4 is a bottom plan view of an absorbent article of this invention in a curved position.

In accordance with the present invention, FIG. 1 illustrates an absorbent article 10 having first and opposite transverse ends 20 and 30, respectively. Absorbent article 10 also has an absorbent structure 40 disposed between a liquid-permeable, body-facing surface 50 and a liquid-impermeable, controlled-deformation shell 60 which includes a garment-facing surface 70 and a pair of lateral sides 80 and 90, respectively.

The shell 60 is preferably formed of a resilient, thermoformable material. The term "resilient" means spontaneously bouncing or springing back into shape, position, etc., after being stretched or bent and the deforming force is removed. Examples of this type of shell are known in Holtman, U.S. Pat. No. 4,685,914, herein incorporated by reference; Baigas, Jr. et al., U.S. Pat. No. 5,013,309; Stern et al., U.S. Pat. No. 4,681,577; Korpman, U.S. Pat. No. 4,554,191; and Menard et al., U.S. Pat. No. 4,740,342. Examples of resilient materials include, without limitation, polymeric foams such as polyethylene foam and polyurethane foam; resilient films; and resilient laminates; and the like. A "controlled-deformation shell" is formed of a resilient material which has structural features to predispose shell deformation when exposed to external forces.

The controlled-deformation nature of the shell 60 is influenced by corrugations, hollows, increased thickness regions, grooves, angles, and the like. One controlled-deformation feature of the present invention is a means for adjusting the length of the garment-facing surface and lateral sides of the shell. The adjusting means 100 can take the form of corrugations, pleats, folds, darts, and the like. Preferably, the adjusting means 100 can allow the length to be increased or decreased.

In a particularly preferred embodiment, the adjusting means includes a plurality of corrugations 100 which are formed in the shell 60. The corrugations 100 have a terminus 110 on the first lateral side 80, radiate toward the garment-facing surface 70, transverse this surface 70, extend up the opposite side 90, and have a second terminus 120 on the opposite side 90. The preferred corrugations 100 have a unique orientation.

The longitudinal distance B between the ridges 131 and 132 of adjacent central corrugations 101 and 102 at their first terminus 111 and 112 is less than the longitudinal distance G between the ridges 131 and 132 of adjacent corrugations 101 and 102 traversing the garment-facing surface 70. Therefore, phantom lines 140, extending from the corrugations 100 on the lateral sides 80 and 90 away from the garment-facing surface 70, converge in a region R beyond the body-facing surface 50.

Distances between additional corrugations 103 disposed adjacent the central corrugations 101 and 102 are not critical. However, the corrugations 103 are arranged such that their terminus 113 on the lateral side 80 is spaced at a longitudinal distance $D_1$ from a central plane P, perpendicular to both the longitudinal axis L of the article and the body-facing surface 50, which is less than the longitudinal distance $D_2$ between the ridge 133 of corrugation 103 at the garment-facing surface 70 and the central plane P.

This is significant, because the garment-facing surface 70 expands and arcs to a greater extent than the body-facing surface 50. Because the longitudinal expansion of the lateral sides 80 and 90 is greater near the garment-facing surface 70 of the shell 60, the chances of the lateral dams 160 buckling and creating side leakage paths is reduced.

The corrugations 100 may have a curvilinear cross section. Examples of such forms include sinusoid, saw-tooth, square wave, or any variation or hybrid of such forms. Of course, these forms may be oriented and focused as described above. The corrugations 100 may be disposed to extend beyond a planar surface defined by the rest of the garment-facing surface 70, or they may be disposed to extend only to that planar surface, or even below the planar surface of the garment-facing surface 70.

While the above discussion and drawings generally refer to the expansion of the corrugations 100, the corrugations 100 may also contract to shorten the garment-facing surface 70. Shortening the garment-facing surface 70 may result in curving the article 10 away from the user's body, at least partially. The garment-facing surface 70 may also be simultaneously shortened in one location or orientation and lengthened in another region or orientation to form an article 10 having complex curves.

There may be any number of corrugations 100 in the shell 60. While the Figures illustrate an embodiment having an even number of corrugations 100, an odd number of corrugations 100 may also be used. If there is an odd number of corrugations 100, the distances B and G between adjacent central corrugations 101 and 102 can be read to describe the distance between a central corrugation 101 and adjacent corrugations 102 on each side. Preferably, there are between about 3 and 25 corrugations, more preferably, about 5 and 7.

When the article 10 is articulated into a curved form, the phantom lines 140 may converge at a focal point F within the convergence region R to provide a radius of curvature for the curved article 10.

A portion of each lateral side 80 and 90 of the shell 60 extends from the garment-facing surface 70 above the plane of this surface 70 and back to the peripheral edge 150 of the shell 60. This portion acts as a dam 160 disposed inward from the peripheral edge 150 to better contain fluids during use. Preferably, the dam 160 is formed in a central region of each lateral side 80 and 90 proximate the peripheral edge 150. Each dam 160 has a first height $H_1$ when the article 10 is in a relatively planar form as depicted in FIG. 5. When the dam 160 is formed only in the central region of each lateral side 80 and 90, the transition between the dam 160 and the peripheral edge 150, both laterally and longitudinally, should be rather smooth. This provides an effective gasketing surface which can intimately contact and seal against the user's perineum and/or adjacent body surfaces to reduce the likelihood of fluid leakage during use. The dam 160 may also extend fully around the body-facing surface 50. The phrase "relatively planar" as used herein the specification and claims means that the described structure is more flat than curved or cupped. When the article 10 is articulated into a cup-like form as illustrated in FIG. 7, the dam 160 acquires a second height $H_2$ which is greater than the first height $H_1$.

The dam 160, peripheral edge 150, absorbent structure 40, and shell 60 cooperate to provide an absorbent article 10 having a structure which resists side leakage failure. During articulation of the article 10, including curving it into a cup-like configuration, the adjusting means 100 permit the garment-facing surface 70 and lateral sides 80 and 90 to expand or contract to relieve stresses induced by curving the article 10, while allowing the dam 160 to remain substantially free of folds and gaps or other imperfections which can lead to side leakage failure. Thus, the surface of the dam 160 maintains an essentially constant perimeter while following body contours, and other portions of the shell 60 adjust to relieve stresses induced by manipulating the article.

Another preferred controlled-deformation feature of the present invention is the use of indentations 170 and 180 in the lateral sides 80 and 90. These indentations 170 and 180 are preferably located proximate the length adjustment means 100. The indentations 170 and 180 allow the shell 60 to deflect in toward the absorbent structure 40 to relieve stresses in the shell 60 without forcing the body facing surface 50 to fold or to gap.

The substantially planar nature of the absorbent article 10 in FIG. 1 allows for ease in manufacturing. It is generally understood in the art that relatively flat articles are easier to cut out, manipulate and package than curved articles. In particular, continuous motion cutting operations can be used to remove the absorbent articles from a conveyed web of multiple articles.

Figure 10:
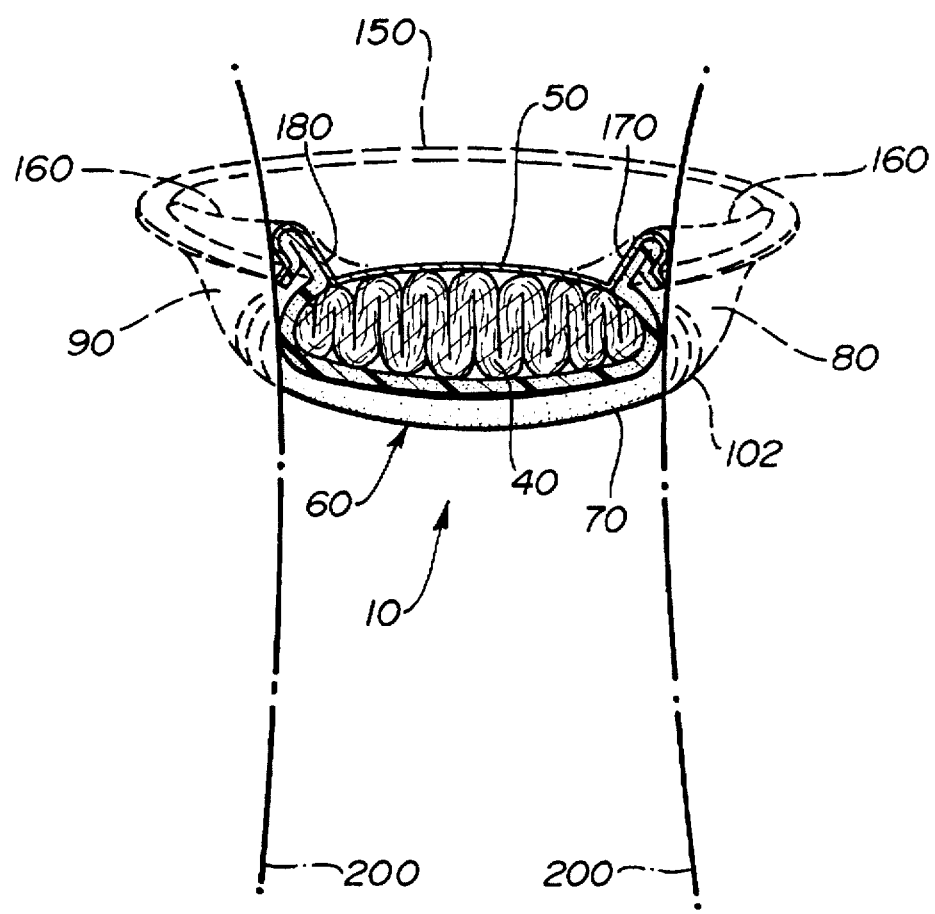
FIG. 10 is a schematic view, similar to FIG. 9, showing an absorbent article of this invention in use.

In use, the absorbent article is placed into a user's undergarment, and may be anchored there by means of a pressure sensitive positioning adhesive or the like. The article is expanded and arced by the force of the user's undergarment and body. In FIG. 2, the arrows pointing to the ends 20 and 30 of the article 10 represent forces articulating the article 10 into a cup-like form. In use, this force is generally supplied by the user's undergarment. The arrows pointing to the peripheral edge 150 proximate the longitudinal center of the article 10 represent forces transversely moving the dams 160 towards each other. This force is generally supplied by the wearer's thighs 200, as illustrated in FIG. 10.

The specification and drawings discussed above are presented to aid in the complete and non-limiting understanding of the invention disclosed herein. Since many variations and embodiments of the invention can be made without departing from its spirit and scope, the invention resides in the claims hereinafter appended.

What is claimed is:

1. An absorbent article useful for wearing in a crotch portion of a user's garment comprising an absorbent structure substantially enclosed by a body-facing liner and a resilient, liquid-impermeable, controlled-deformation shell; wherein the liquid-impermeable shell comprises (a) a peripheral edge, (b) longitudinal ends and lateral sides extending away from the body-facing liner proximate the peripheral edge to a garment-facing surface and (C) means for adjusting the length of the garment-facing surface and lateral sides, wherein said means originates at at least one point on one of said lateral sides, each of said at least one point being spaced from said peripheral edge, said means extends towards and across said garment-facing surface, and terminates at at least one second point on the other of said lateral sides, said at least one second point being spaced from said peripheral edge; whereby the garment-facing surface and lateral sides of the shell can expand or contract to relieve stresses induced by curving the article while allowing the body-facing liner to form a substantially smooth curve and to remain substantially free of folds.

2. The absorbent article of claim 1 wherein the controlled-deformation shell comprises a thermoformable material.

3. The absorbent article of claim 2 wherein the thermoformable material comprises a polymeric foam.

4. The absorbent article of claim 2 wherein the thermoformable material comprises a polymeric film structure.

5. The absorbent article of claim 1 wherein the means for adjusting the length of the garment-facing surface and lateral sides comprises a plurality of transversely extending corrugations having a terminus on one of the lateral sides, radiating toward the garment-facing surface, traversing the garment-facing surface, and having a second terminus on the opposite lateral side.

6. An absorbent article useful for wearing in a crotch portion of a user's garment comprising an absorbent structure disposed between a liquid permeable, body-facing surface and a resilient, liquid-impervious, controlled-deformation shell; wherein the shell has a pair of oppositely disposed lateral sides and a garment-facing surface; the body-facing surface and shell are attached about a periphery; the shell has a plurality of transversely extending corrugations, which corrugations have a terminus on one of the lateral sides, radiate toward the garment-facing surface, and have a second terminus on the opposite lateral side; phantom lines extending from the corrugations on the lateral sides, in the direction of the corrugations and away from the garment-facing surface, converge in a region beyond the body-facing surface of the article; and the garment-facing surface of the shell is capable of articulating from a relatively planar form to an arcuate form.

7. The absorbent article of claim 6 wherein a longitudinal distance from a terminus of a transverse corrugation to a central plane, perpendicular to the planar form of the garment-facing surface and to a longitudinal axis of the article, is less than a longitudinal distance from the central plane to that corrugation at the garment-facing surface of the shell.

8. The absorbent article of claim 6 wherein there is an even number of transverse corrugations.

9. The absorbent article of claim 6 wherein there is an odd number of transverse corrugations.

10. The absorbent article of claim 6 wherein the shell is formed of a thermoformable material.

11. The absorbent article of claim 10 wherein the thermoformable material comprises a polymeric foam.

12. The absorbent article of claim 10 wherein the thermoformable material comprises a polymeric film structure.

13. The absorbent article of claim 6 wherein the arcuate form is a curved form having a radius of curvature from a focal point in the convergence region.

14. The absorbent article of claim 13 wherein the phantom lines converge at the focal point in the curved form.

15. The absorbent article of claim 6 which is a sanitary napkin.

16. The absorbent article of claim 6 which is an adult incontinence article.

17. An absorbent article useful for wearing in a crotch portion of a user's garment comprising an absorbent structure substantially enclosed by a body-facing liner generally defining a plane and a resilient, liquid-impermeable, controlled-deformation shell; the liquid-impermeable shell comprising (a) a peripheral edge, (b) longitudinal ends and lateral sides extending away from the body-facing liner proximate the peripheral edge to a garment-facing surface and (C) means for adjusting the length of the garment-facing surface and lateral sides, wherein said means originates at at least one point on one of said lateral sides each of said at least one point being spaced from said peripheral edge, said means extends towards and across said garment-facing surface, and terminates at at least one second point on the other of said lateral sides, said at least one second point being spaced from said peripheral edge; wherein a portion of each lateral side of the shell extends from the garment-facing surface above a plane formed by the body-facing liner proximate the peripheral edge to form a dam disposed inward from the peripheral edge; whereby the garment-facing surface and lateral sides of the shell can expand or contract to relieve stresses induced by curving the article while allowing the body-facing liner to form a substantially smooth curve and to remain substantially free of folds.

18. The absorbent article of claim 17 wherein the shell comprises a thermoformable material.

19. The absorbent article of claim 18 wherein the thermoformable material comprises a polymeric foam.

20. The absorbent article of claim 18 wherein the thermoformable material comprises a polymeric film structure.

21. The absorbent article of claim 17 wherein the dam is formed in a central region of each lateral side proximate the peripheral edge.

22. The absorbent article of claim 17 wherein the dam has a first height when the absorbent article has a relatively planar form, and the dam acquires a second height, greater than the first height, when the absorbent article is articulated into a curved form.

23. The absorbent article of claim 17 which is a sanitary napkin.

24. The absorbent article of claim 17 which is an adult incontinence article.

25. An absorbent article useful for wearing in a crotch portion of a user's garment comprising an absorbent structure disposed between a liquid permeable, body-facing surface and a resilient, liquid-impervious, controlled-deformation shell; wherein the shell has a pair of oppositely disposed lateral sides, a garment-facing surface and a peripheral edge; the body-facing surface and shell are attached about the peripheral edge of the shell; a portion of each lateral side of the shell extends from the garment-facing surface above a plane formed by the body-facing liner proximate the peripheral edge to form a dam disposed inward from the peripheral edge; the shell has a plurality of transversely extending corrugations which have a terminus on one of the lateral sides, radiate toward the garment-facing surface, traverse the garment-facing surface, and have a second terminus on the opposite lateral side; phantom lines extending from the corrugations on the lateral sides, in the direction of the corrugations and away from the garment-facing surface, converge in a region beyond the body-facing surface of the article; and the garment-facing surface of the shell is capable of articulating from a relatively planar form to an arcuate form.

26. The absorbent article of claim 25 wherein the arcuate form is a curved form having a radius of curvature from a focal point in the convergence region.

27. The absorbent article of claim 26 wherein the phantom lines converge at the focal point in the curved form.

28. The absorbent article of claim 25 wherein the dam is formed in a central region of each lateral side proximate the peripheral edge.

29. The absorbent article of claim 25 wherein the dam has a first height when the absorbent article has a relatively planar form, and the dam acquires a second height, greater than the first height, when the absorbent article is articulated into a curved form.

30. The absorbent article of claim 25 which is a sanitary napkin.

31. The absorbent article of claim 25 which is an adult incontinence article.

32. An absorbent article useful for wearing in a crotch portion of a user's garment comprising an absorbent structure substantially enclosed by a body-facing liner and a resilient, liquid-impermeable, controlled-deformation shell; wherein the liquid-impermeable shell comprises (a) a peripheral edge, (b) longitudinal ends and lateral sides extending away from the body-facing liner proximate the peripheral edge to a garment-facing surface and (c) means for adjusting the length of the garment-facing surface and lateral sides, wherein said means originates at at least one point on one of said lateral sides, each of said at least one point being spaced from said peripheral edge, said means extends towards and across said garment-facing surface, and terminates at at least one second point on the other of said lateral sides, said at least one second point being spaced from said peripheral edge, (d) and an indentation along the lateral sides proximate the adjusting means; whereby the garment-facing surface and lateral sides of the shell can expand or contract to relieve stresses induced by curving the article while allowing the body-facing liner to form a substantially smooth curve and to remain substantially free of folds.

* * * * *